(12) United States Patent
Ranallo et al.

(10) Patent No.: US 7,759,106 B2
(45) Date of Patent: Jul. 20, 2010

(54) **CONSTRUCTION OF LIVE ATTENUATED *SHIGELLA* VACCINE STRAINS THAT EXPRESS CFA/I ANTIGENS (CFAB AND CFAE) AND THE B SUBUNIT OF HEAT-LABILE ENTEROTOXIN (LTB) FROM ENTEROTOXIGENIC *E. COLI***

(75) Inventors: Ryan T. Ranallo, Gaithersburg, MD (US); Malabi M. Venkatesan, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 801 days.

(21) Appl. No.: 11/132,199

(22) Filed: May 19, 2005

(65) Prior Publication Data

US 2007/0237791 A1 Oct. 11, 2007

Related U.S. Application Data

(60) Provisional application No. 60/575,719, filed on May 19, 2004.

(51) Int. Cl.
*C12N 1/20* (2006.01)
*C12P 21/06* (2006.01)
*A61K 39/02* (2006.01)
*A61K 39/38* (2006.01)
*A61K 45/00* (2006.01)

(52) U.S. Cl. ............... 435/252.3; 435/69.1; 424/234.1; 424/184.1; 424/278.1

(58) Field of Classification Search ............... 435/69.1, 435/252.3; 424/234.1, 184.1, 278.1
See application file for complete search history.

(56) References Cited

FOREIGN PATENT DOCUMENTS

EP 0 265 244 4/1988
WO WO 03/022307 A1 3/2003

OTHER PUBLICATIONS

Anja M. Hamers et al, "The Nucleotide Sequence of the First Two Genes of the CFA/1 Fimbrial Operon of Human Enterotoxigenic *Escherichia coli*," Microbial Pathogenesis 1989, No. 6, pp. 297-309.
Geraldine A. Willshaw et al, "Cloning of Regions Encoding Colonisation Factor Antigen 1 and Heat-Stable Enterotoxin in *Escherichia coli*," FEMS Microbiology Letters, No. 16 1983, pp. 101-106.
Ryan T. Ranallo et al, "Construction and Chracterization of Bivalent *Shigella flexneri* 2a Vaccine Strains SC608(pCFAIi) and SC608(pCFAI/LTB) That Express Antigens from Enterotoxigenic *Escherichia coli*" American Society for Microbiology, Infection and Immunity, vol. 73, No. 1, Jan. 2005, pp. 258-267.
Bart J.A.M. Jordi et al, "The Complete Nucleotide Sequence of Region 1 of the CFA/I Fimbrial Operon of Human Enterotoxigenic *Escherichia coli*" DNA Sequences, J. DNA Sequencing and Mapping, vol. 2, pp. 257-263.
Paul H. M. Savelkoul et al., Expression of CFA/I Fimbriae is Positively Regulated, Microbial Pathogenesis 1990, No. 8, pp. 91-99.
Roy Curtiss III et al., "Recombinant Avirulent *Salmonella* Vaccine Strains with Stable Maintenance and High Level Expression of Cloned Genes in Vivo," Immunological Investigations, No. 18 (1-4), 1989, pp. 583-596.
Hilary Koprowski II et al, "Attenuated *Shigella flexneri* 2a Vaccine Strain CVD 1204 Expressing Colonization Factor Antigen I and Mutant Heat-Labile Enterotoxin of Enterotoxigenic *Escherichia coli*," Infection and Immunity, vol. 68, No. 9, Sep. 2000, pp. 4884-4892.
Shaguang Wu et al, "Immune Responses to Novel *Escherichia coli* and *Sallmonella typhimurium* Vectors that Express Colonization Factor Antigen I (CFA/I) of Enterotoxigenic *E. coli* in the Absence of the CFA/I Position Regulator *cfa*R," Infection and Immunity, vol. 63, No. 12, Dec. 1995, pp. 4933-4938.

*Primary Examiner*—Robert B Mondesi
*Assistant Examiner*—Lakia J Tongue
(74) *Attorney, Agent, or Firm*—Elizabeth Arwine

(57) ABSTRACT

With the goal of creating a combination vaccine against *Shigella* and other diarrheal pathogens we have constructed a prototype vaccine strain of *Shigella flexneri* 2a (SC608) that can serve as a vector for the expression and delivery of heterologous antigens to the mucosal immune system. SC608 is an asd derivative of SC602, a well-characterized vaccine strain, which has recently undergone several phase 1 and 2 trials for safety and immunogenicity. Using non-antibiotic asd-based plasmids, we have created novel constructs for the expression of antigens from enterotoxigenic *E. coli* (ETEC), including CFA/I (CfaB and CfaE) and the B-subunit from heat-labile enterotoxin (LTB) in *Shigella* vaccine strain SC608. Heterologous protein expression levels and cellular localization are critical to immune recognition and have been verified by immunoblot analysis. Following intranasal immunization (SC608(CFAI) and SC608(CFAI/LTB) of guinea pigs, serum IgG and IgA immune responses to both the *Shigella* LPS and ETEC antigens can be detected by ELISA. In addition, ELISPOT analysis for ASCs from cervical lymph nodes and spleen showed similar responses. All vaccine strains conferred high levels of protection against challenge with wild-type *S. flexneri* 2a using the Sereny test. Furthermore, serum from guinea pigs immunized with SC608 expressing CfaB and LTB contained antibodies capable of neutralizing the cytological affects of heat-labile toxin (HLT) on Chinese Hamster Ovary (CHO) cells. These initial experiments demonstrate the validity of a multivalent invasive *Shigella* strain that can serve as a vector for the delivery of pathogen-derived antigens.

8 Claims, 9 Drawing Sheets

MW  1  2  3  4  5

207
129

85

39
32

17    ← CfaB

7

α CFA/I
WESTERN

21    ← LTB

6

α HLT
WESTERN

FIG. 2B

FIG. 5C HLT+NS
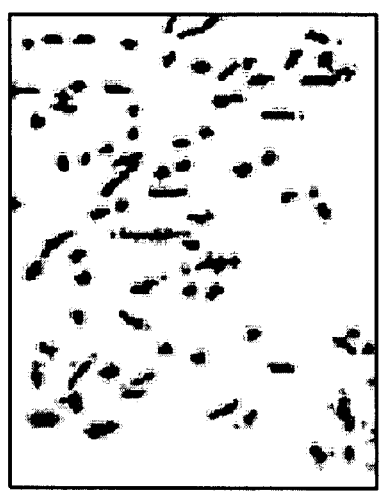
FIG. 5F HLT+SC608(CFAI/LTB)
FIG. 5B HLT
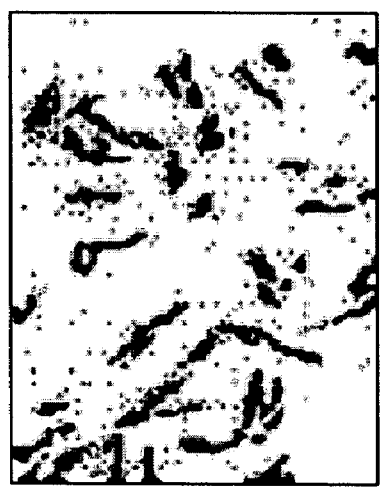
FIG. 5E HLT+SC608(CFAI)
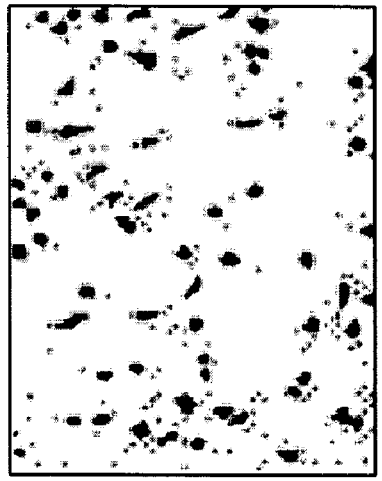
FIG. 5A PBS
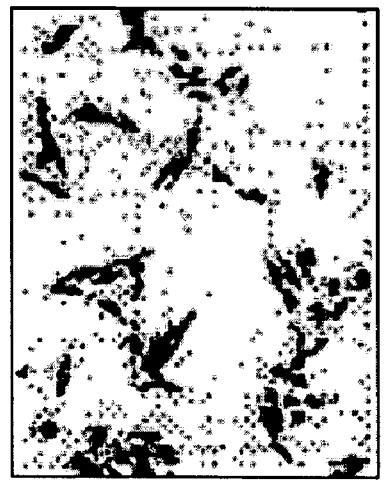
FIG. 5D HLT+SC608(3098)

```
SEQUENCE LISTING

<160> NUMBER OF SEQ ID NOS: 10

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
gatcaagctt ccatgaaaaa ggagggatgt a                                      31

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 2
gatcccatgg gcatgcataa attattctat ttactaagt                              39

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer
```

```
<400> SEQUENCE: 3
tacatgccat ggataaatta ttctatttac t                                    31

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 4
attctgttat atatgtcaac ctgcaggagg gatgtataaa catacc                    46

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 5
ggtatgttta tacatccctc ctgcaggttg acatatataa cagaat                    46

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
ttacccaagc ttagacatgc ttttaaagca aa                                   32

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
tacatgccat ggataaatta ttctatttac t                                    31

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 8
cgtttatcct ttatcattct cttagtatat agatgagtaa                           40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 9
ttactcatct atatactaag agaatgataa aggataaacg                           40

<210> SEQ ID NO 10
```

```
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 10
ttcagcccaa gctttagcgc caatatgttg ttat                             34
```

CONSTRUCTION OF LIVE ATTENUATED *SHIGELLA* VACCINE STRAINS THAT EXPRESS CFA/I ANTIGENS (CFAB AND CFAE) AND THE B SUBUNIT OF HEAT-LABILE ENTEROTOXIN (LTB) FROM ENTEROTOXIGENIC *E. COLI*

CROSS-REFERENCE TO RELATED APPLICATION

This application claims the benefit of U.S. Provisional Application No. 60/575,719, filed May 19, 2004. The content of this application is expressly incorporated herein by reference.

FIELD OF INVENTION

The invention relates to materials and methodologies for preparing multivalent vaccines, recombinant DNA expression products and more particularly to vector constructs which effectively express the cfaB, cfaE and LTB proteins in *Shigella* spp. without affecting the ability of the *Shigella* strain to invade cells of the colonic epithelium following oral administration to humans.

BACKGROUND OF THE INVENTION

Diarrheal diseases are a significant global problem resulting in high levels of morbidity and mortality especially to children under the age of 5. Two of the most prominent agents that cause diarrheal disease are *Shigella* spp and enterotoxigenic *E. coli*. (ETEC). Current measures for preventing and treating these diseases are insufficient in that over 375 million cases occur with an estimated 1.48 million resulting in death annually (34).

*Shigella* spp are invasive pathogens that can cause disease through ingestion of food or water contaminated with as little as 100 bacteria. *Shigella* can penetrate the intestinal epithelial cells of the colonic mucosa and stimulate a mucosal inflammatory response eliciting the production of an array of proinflammatory cytokines leading to recruitment of neutrophils and macrophages (reviewed in (15)). Following invasion, the bacteria multiply and spread to contiguous cells using actin polymerization (25). The resulting disease shigellosis (bacillary dysentery) is characterized by an inflammatory condition of the colon with accompanying fever, vomiting, severe abdominal pain, diarrhea and passage of blood and mucus-containing stools (13).

Enterotoxigenic *E. coli* (ETEC) is also transmitted through contaminated food or water, however the infectious dose for ETEC is much higher (11). Once ingested, ETEC attach to mucosal epithelial cells using proteinacious fimbriae or colonization factor antigens (CFAs or CFs) and can secrete up to two separate enterotoxins designated heat-stable toxin (ST) and heat-labile toxin (HLT) (reviewed in (19) and refs therein). Immune response to ETEC infections indicates secretory IgA (sIgA) directed towards CFs can provide protective immunity against homologous fimbrial type (11).

Currently, there is a significant effort being put forth toward the development of a safe and efficacious vaccine for both of these enteric diseases. These efforts include: subcellular complexes purified from virulent *Shigella* (30), detoxified LPS-conjugates, subunit approaches, killed whole-cell preparations, and attenuation of pathogenic isolates for use as live attenuated vaccines (34).

Precise or targeted attenuation of pathogenic (invasive) strains of *Shigella* has made significant progress over the past 15 years. Initially attenuating mutations were made in key biosynthetic pathways creating auxotrophic mutants, which maintain the invasive nature of *Shigella*. These mutations tended to reduce or eliminate intracellular replication once inside the host cytoplasm. However, a greater understanding of the molecular pathogenesis of *Shigella* has led to the targeting of specific virulence factors (24) and reviewed in (15). One such strain, SC602 has deletions in both IcsA and IucA (6). This strain is highly invasive, however once inside host cells it cannot spread to contiguous cells due to the IcsA mutation. IcsA mutants, unlike wild-type strains, do not elicit a characteristic keratoconjunctivitis (Sereny reaction) when applied to the eyes of guinea pigs, SC602 has recently undergone phase 1 and 2 clinical trials in North American volunteers and demonstrated significant protection against severe shigellosis (7, 20). However, the vaccine can be reactogenic at doses higher than $10^4$ thus demonstrating the need to balance attenuation with immunogenicity.

In addition to their potential for protection against shigellosis, attenuated strains of *Shigella* have been used as delivery vehicles for genes encoding numerous other protective antigens (1, 3-6, 21, 23). In one scenario the heterologous genes are regulated using a prokaryotic promoter and expressed by the attenuated bacteria. Immunogenicity of the antigen in this situation depends on the subcellular location and of the antigen within the bacteria (17, 22). The heterologous antigen is then processed by the immune system along with other bacterially derived antigens. Alternatively, the bacteria harbor heterologous genes under the control of a eukaryotic promoter. These so-called DNA vaccines are delivered to antigen presenting cell (APCs) following invasion and bacterial lysis. Once inside the APC the eukaryotic promoter is turned on and the expression of foreign proteins leads to an immune response (reviewed in (32)). Regarding the former scenario several considerations must be considered when expressing pathogen-derived heterologous protein antigens in attenuated bacterial vectors regardless of the antigen and species of bacteria. First, the antigen must be expressed at optimum level so as to minimize further attenuation of the vaccine strain. The second consideration is the cellular location and thus presentation to the immune system. A comparative study looking at antigen subcellular location (periplasmic or secreted vs. cytoplasmic) found that periplasmic and extracellular antigens are more immunogenic that antigens retained in the cytoplasm (17). Finally, the goal is to create a multivalent vaccine strain and thus heterologous antigen expression should not reduce the immunogenicity (invasiveness) of the bacterial vector.

There are several reports of *Shigella* being used as a carrier of both heterologous protein and DNA antigens. In particular, the Center for Vaccine Development (CVD) of the University of Maryland School of Medicine has set out and made significant progress towards the goal of constructing a combination vaccine to protect against *Shigella* and ETEC-associated diarrhea (1, 2, 4, 21, 23). They have used the engineered *Shigella* vaccine strain CVD 1204 (ΔguaBA) to express several ETEC fimbrial antigens as well as mutant heat-labile toxin (mLT) (1, 2, 4, 21). The CVD's approach has been to clone and express the entire fimbrial operon under the control of an inducible promoter. To date they have constructed and tested *Shigella* strains that express CFA/I, CS2, CS3, CS4, as well as detoxified mLT (LThK63 or LThR72). Guinea pigs immunized with mixed inoculums containing five different *Shigella* strains, each expressing individual ETEC fimbriae, showed serum and mucosal antibody responses to both the *Shigella* vector and the ETEC fimbriae (4).

SUMMARY OF THE INVENTION

The invention includes primer pairs characterized as having a length of about 15-100 nucleotides, preferably between 25-75 nucleotides, most preferably 30-46 nucleotides, which pairs permit the PCR amplification of the entire CfaA, CfaB and CfaE open reading frames without the entire CFA/I operon but with the signal sequence of each protein along with restriction sites for insertion into a vector which insertion allows for expression, export and assembly of the protein on the bacterial surface. The primer pairs are grouped as follows:
 a) 5'-GATCAAGCTTCCATGAAAAAGGAGGGAT-GTA-3' [SEQ ID NO 1] and 5'-GATCCCATGGGCAT-GCATAAATTATTCTATTTACTAAGT-3' [SEQ ID NO 2]
 b) 5'-TACATGCCATGGATAAATTATTCTATTTACT-3' [SEQ ID NO 3] and 5'-ATTCTGTTATATATGTCAAC-CTGCAGGAGGGATGTATAAACATACC-'3 [SEQ ID NO 4],
 c) 5'-GGTATGTTTATACATCCCTCCTGCAGGT-TGACATATATAACAGAAT-3' [SEQ ID NO 5] and 5'-TTACCCAAGCTTAGACATGCTTTTAAAG-CAAA-3' [SEQ ID NO 6] and
 d) 5'-TACATGCCATGGATAAATTATTCTATTTACT-3' [SEQ ID NO 7] and 5'-CGTTTATCCTTTATCAT-TCTCTTAGTATATAGATGAGTAA-3' [SEQ ID NO 8] and
 e) 5'-TTACTCATCTATATACTAAGAGAAT-GATAAAGGATAAACG-3' [SEQ ID NO 9] and 5'-TTCAGCCCAAGCTTTAGCGCCAATATGT-TGTTAT-3' [SEQ ID NO 10].

A further embodiment of the invention are vectors containing a cis-acting DNA promoter element capable of initiating the synthesis of mRNA operabley linked to an open reading frame containing one or more ETEC genes. ETEC genes of interest include cfaA, cfaB, cfaE, LTh B, (LTB). The vector is designed so that the entire CfaA, CfaB and CfaE open reading frames is expressed without the entire CFA/I operon. The resultant protein is exported and assembled on the bacterial surface. A conventional cis-acting promoter suitable for use in the invention is Ptrc. The exemplified vectors include plasmid pCFAI, pCFAI/LTB, and pCfaAE. These plasmids are derived from pYA3098. It should be noted that these vectors do not contain a gene that produces a product capable of breaking down any formally declared antimicrobial agent for the exclusive purpose of maintaining the vector. There is no antibiotic marker. The vector population can be maintained without the use of antibiotics.

The open reading frame can contain a chaperone-subunit consisting essentially of CfaA-CfaB or CfaA-CfaE and results in periplasmic accumulation of both the major and minor subunits from CFA/I. (A chaperone-subunit combination is an interaction between two proteins whereby the charperone enables the correct folding and stabilization of the subunit. The subunit here is a protein product that constituents a fimbriae from enterotoxigenic *E. coli*.)

The vectors of the invention can also contain the cfaABCE gene cluster from enterotoxigenic *E. coli* H10407. This open reading frame can also include CS6, CS3 and CS17 (Enterotoxigenic *E. coli* strains).

The open reading frame typically contains a single linear DNA fragment encoding the cfaA, cfaB, cfaE and LTh B (LTB) genes. This fragment is obtained by the PCR amplification using the primers of the invention.

A further embodiment of the invention are the use of the vectors to transform *Shigella* species which results in the periplasmic expression of heterologous antigens. This expression is not likely to alter either *Shigella*'s natural tissue tropism (colonic epithelium) following oral immunization or significantly reduce strains invasiveness. Suitable *Shigella* species include *S. sonnei*, *S. dysenteriae* and *S. flexner*, in particular *S. sonnei* WRSs1 and *S. dysentariae* WRSd1. Exemplified transformed *shigella* strains include *Shigella* vaccine strain, e.g. *Shigella flexnari*. 2a (SC608) (3098), *Shigella flexnari* 2a (SC608) (LTB), *Shigella flexnari* 2a (SC608) (CFAI) and *Shigella flexnari* 2a (SC608) (CFAI/LTB). These strains are characterized as having deletions in icsA which causes intracellular spreading of bacteria to contiguous host epithelial cells.

These transformed *shigella* strains are suitable for use in immunogenic composition, in particular vaccines. The vaccines are adapted for oral or mucosal administration. The vaccines induce a protective immune response and are suitable for the treatment of *Shigella* or ETEC-mediated Traveler's Diarrhea. the protective immune response is directed toward *Shigella* and ETEC. The immune response is directed to both *Shigella* LPS heterologous antigen and is measurable in serum, cervical lymph nodes, spleen or other mucosal surface.

The vaccines can be characterize as multivalent vaccine, e.g. bivalent vaccine. The *Shigella* can be either live or attenuated. The vaccine can be administered to the subject in one or a series of does over time.

In summary, the invention has as its goal the creation of a combination vaccine against *Shigella* and other diarrheal pathogens. A prototype vaccine strain of *Shigella flexneri* 2a (SC608) was constructed that can serve as a vector for the expression and delivery of heterologous antigens to the mucosal immune system. SC608 is an asd derivative of SC602, a well-characterized vaccine strain, which has recently undergone several phase 1 and 2 trials for safety and immunogenicity. Using non-antibiotic asd-based plasmids, a novel constructs were created for the expression of antigens from enterotoxigenic *E. coli* (ETEC), including CFA/I (CfaB and CfaE) and the B-subunit from heat-labile enterotoxin (LTB) in *Shigella* vaccine strain SC608. Heterologous protein expression levels and cellular localization are critical to immune recognition and have been verified by immunoblot analysis. Following intranasal immunization (SC608(CFAI) and SC608(CFAI/LTB) of guinea pigs, serum IgG and IgA immune responses to both the *Shigella* LPS and ETEC antigens can be detected by ELISA. In addition, ELISPOT analysis for ASCs from cervical lymph nodes and spleen showed similar responses. All vaccine strains conferred high levels of protection against challenge with wild-type *S. flexneri* 2a using the Sereny test. Furthermore, serum from guinea pigs immunized with SC608 expressing CfaB and LTB contained antibodies capable of neutralizing the cytological affects of heat-labile toxin (HLT) on Chinese Hamster Ovary (CHO) cells. These initial experiments demonstrate the validity of a multivalent invasive *Shigella* strain that can serve as a vector for the delivery of pathogen-derived antigens.

BRIEF DESCRIPTION OF THE DRAWINGS

FIG. 2A shows Western blot probed with rabbit anti-CFA/I. FIG. 2B shows Western blot probed with rabbit anti-HLT. Lane 1, SC608(3098), lane 2, SC608(CFAI), Lane 3, SC608(CFAI/LTB), Lane 4, purified CFA/I fimbriae, Lane 5, purified HLT.

FIGS. 4 A and B show the reaction to *S. flexneri* 2a LPS, CFA/I, or HLT was measured in serum and FIG. 4 C shows mucosal secretions by ELISA. The bars represent the mean OD595±standard error (y axis) for each vaccination group (x axis) consisting of 8 individual guinea pigs. The number of animals responding is indicated above some bars. Isotype, antigen, and dilution factors are indicated on top and immunizing strain is indicated on the bottom of each graph.

FIG. 5 A shows CHO cells treated with PBS. FIG. 5 B shows CHO cells treated with HLT (25 ng/ml). FIG. 5 D shows CHO cells treated with HLT+SC608(3098). FIG. 5 E shows CHO cells treated with HLT+SC608(CFAI). FIG. 5 F shows CHO cells treated with HLT+SC608(CFAI/LTB). FIG. 5 shows a graph where inhibition is plotted against serum dilution. Antiserum was serially diluted in PBS and mixed with a constant amount (25 ng/ml) of HLT. Percent inhibition was calculated by taking elongation with 25 ng/ml HLT alone as 100% elongation.

DETAILED DESCRIPTION OF THE INVENTION

The invention is directed to a unique approach for creating a bivalent vaccine that uses *Shigella flexneri* 2a (strain SC608) as vector to carry ETEC antigens to the mucosal immune system. ETEC antigens are incorporated into SC608 by employing a plasmid-based aspartate semialdehyde dehydrogenase (asd) 'balanced-lethal' system developed by Roy Curtiss III and colleagues (8). An asd mutant of *Shigella flexneri* 2a (SC602), called SC608 was created and used to express antigens from ETEC including the CFA/1 major subunit, CfaB, CFA/1 minor subunit CfaE and the B-subunit from the type I heat-labile toxin (LTB). The expression plasmids for CfaB, CfaE and LTB represent a novel method for fimbrial antigen expression. The chaperone-subunit (CfaA-CfaB and CfaA-CfaE) combination in each of the expression plasmids allows for periplasmic accumulation of both the major and minor subunits from CFA/I. This represents a novel configuration and provides a strategy for the construction of expression plasmids for other colonization factor antigens.

Heterologous protein expression levels are critical to immune recognition and have been verified by immunoblot analysis for all three expression plasmids. Strain invasiveness, a phenotype critical for the induction of an effective immune response, was confirmed using HeLa cell invasion with gentamicin protection. Immunogenicity experiments for SC608(pCFAI) and SC608(pCFAI/LTB) were assessed following intranasal immunization of guinea pigs. Serum and mucosal secretion were positive for both *Shigella flexneri* 2a LPS and ETEC antigens CFAI and LTB. In addition, ELISPOT analysis for antibody secreting cells from cervical lymph nodes and spleens correlated with the ELISA results. All immunized guinea pig were protected from severe conjunctivitis using the Sereny test. Finally, we have used in vitro assays to examine the specificity of the antibodies generated against ETEC antigens.

Figure 1A:
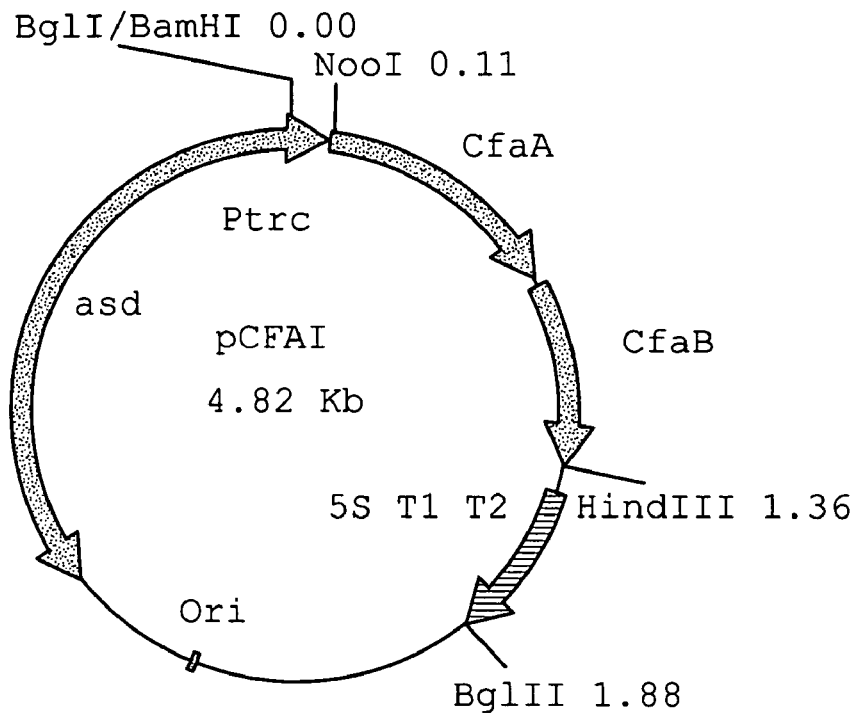
FIGS. 1A and B show a diagram of asd-based plasmids pCFAI and, pCFAI/LTB respectively. The map of each plasmids including, restriction sites approximate locations, genes and origin of replication are indicated.
Figure 1B:
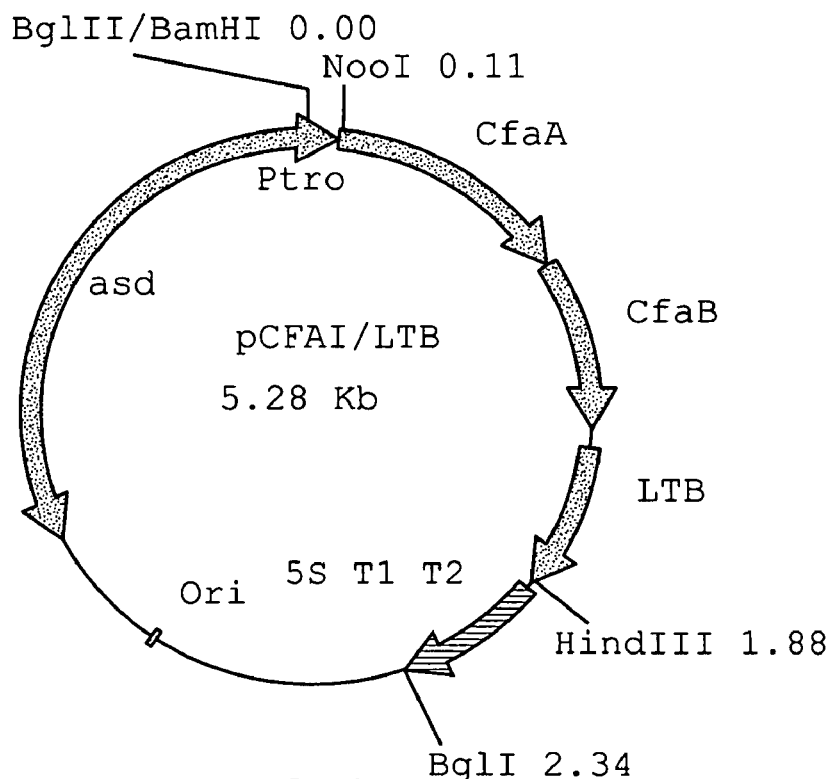

Cloning of CFA/I and LTB Expression Constructs:

The cfaABCE gene cluster from enterotoxigenic *E. coli* (ETEC) H 10407 (16) was used to design primers for PCR amplification of the entire CfaA, CfaB and CfaE open reading frames (ORFs). The primers were designed to include the signal sequence of each protein as well as restriction sites allowing for insertion into the asd-based vector pYA3098 (gift from Roy Curtiss III) down stream from the Ptrc promoter. The resulting clones (pCFAI and pCfaAE) are unique constructs for the expression of CfaB and CfaE (FIGS. 1A, 1C). Previous constructs employed for heterologous CFA/I expression in *Shigella* and *Salmonella* have included the entire CFA/I operon, allowing for not only expression, but also export and assembly of CFA/I fimbriae on the bacterial surface. We have chosen a different strategy for expressing ETEC fimbrial proteins in *Shigella* for several reasons. First, periplasmic expression of heterologous antigens is not likely to alter *Shigella*'s natural tissue tropism (colonic epithelium) following oral immunization. Second, this type of expression doesn't significantly reduce strains invasiveness (data not shown and FIG. 2E), a property that is likely necessary for induction of protective immune responses. In an attempt to create a more comprehensive *Shigella*-ETEC hybrid strain we generated a second construct, which included the B subunit of heat labile toxin (LTB) from ETEC. The eltB or LThB gene sequence, encoding LTB, was used to design PCR primers for amplification of the LTB ORF. A second round of PCR was used to create a single DNA fragment containing the CfaA, CfaB, and LTB ORFS. This DNA fragment was inserted into pYA3098 down stream of the Ptrc promoter, creating the plasmid pCFAI/LTB (FIG. 1B).

Protein Expression of ETEC Antigens in *Shigella* Vaccine Strain SC608:

The asd 'balance-lethal' system, which allows for selection of a plasmid without antibiotic resistance genes, (12, 18, 33), was used to express antigens derived from ETEC in *Shigella*. SC602 was used to create an asd mutant (SC608), which when grown in LB medium has an obligate growth requirement for diaminopimelic acid (DAP) unless complemented with an asd-containing plasmid. The expression plasmids (pCFAI, pCfaAE and pCFAI/LTB), along with an empty vector control (pYA3098), were electroporated into SC608, generating the *Shigella* vaccine strains SC608(3098), SC608 (CFAI), SC608(CfaAE) and SC608(CFAI/LTB).

Figure 2C:
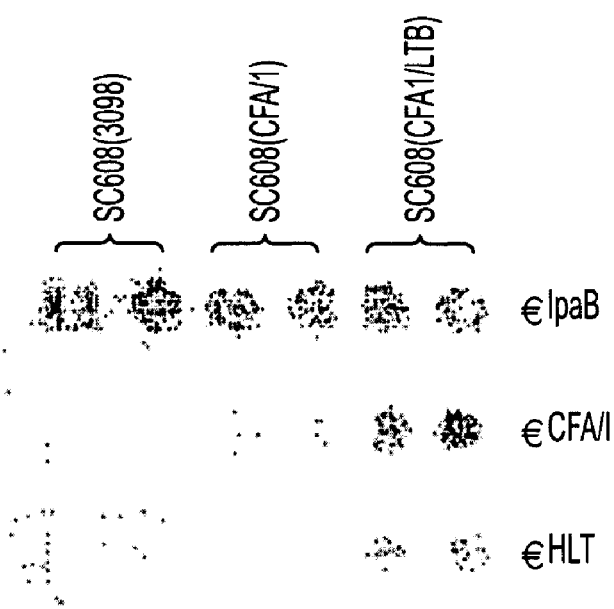
FIG. 2C shows Colony immunoblots. The indicated colonies were spotted in duplicate, lifted to nitrocellulose, washed extensively and probed with the indicated rabbit polyclonal antibody. HeLa cell invasion assay. *Shigella* vaccine strains were tested for the ability to invade HeLa epithelia cells using the gentamicin protection assay.

CfaB expression in these new strains was initially evaluated in whole-cell extracts prepared from log phase cultures. Immunoblotting using CFA/I-specific antiserum generated against intact fmbrae demonstrated that both SC608(CFAI) and SC608(CFAI/LTB) were expressing nearly equivalent amount of the 15-kDa CfaB protein (FIG. 2A, compare lanes 2 and 3). In order to demonstrate expression of LTB, the same extracts were separated on a 4-12% SDS-polyacrylamide gel and transferred to nitrocellulose. Immunoblotting using antiserum to E. coli type I heat-labile toxin (HLT) detected a ~12-kDa band corresponding to LTB in the extracts of SC608 (CFAI/LTB) only (FIG. 2B, lane 3). No band of this mass was detected in the lanes of the controls strains that lack the LTB ORF (FIG. 1B, lanes 1 and 2). CfaE expression was also evaluated in whole-cell extracts prepared from log phase cultures. Immunoblotting using CfaE-specific antiserum demonstrated that both two individual colonies of SC608 (CfaAE) were expressing the CfaE protein (FIG. 2C lanes 2 and 3).

Previous studies using *Salmonella* as mucosal delivery vector have indicated that antigens located in the periplasm and extracellular fluid are much more immunogenic than antigens retained in the cytoplasm (17). Having modified the CFA/I operon in our expression constructs we sought to examine the subcellular location of CfaB and LTB using a simple colony blot technique (28). The technique allows for the absorption of extracellular and perhaps periplasmic proteins directly to nitrocellulose for detection. As a control all vaccine strains were evaluated for the expression of IpaB, a *Shigella* protein critical for the invasion phenotype (FIG. 2C). All strains had similar levels of IpaB, while only SC608 (CFAI) and SC608(CFAI/LTB) were positive for CfaB (FIG. 2C). Interestingly, SC608(CFAI) had slightly reduced levels of CfaB as compared to SC608(CFAI/LTB) in the colony blot, but very similar levels in whole cell extracts (compare FIGS. 2A and 2C). As expected, only SC608(LTB) was positive for LTB expression (FIG. 2C). Similar experiments where colonies are treated briefly (3 min.) with lysozyme yields the same result with a slightly stronger signal (data not shown). Thus by western and colony immunoblotting we can show expression of CfaB using the modified CFA/I operon lacking the cfaC and cfaE. Furthermore we show that replacement of these genes with LTB allows for the expression of both CfaB and LTB using a single Ptrc promoter. Periplasmic expression of CfaE was demonstrated using identical protocols (data not shown).

Figure 2D:
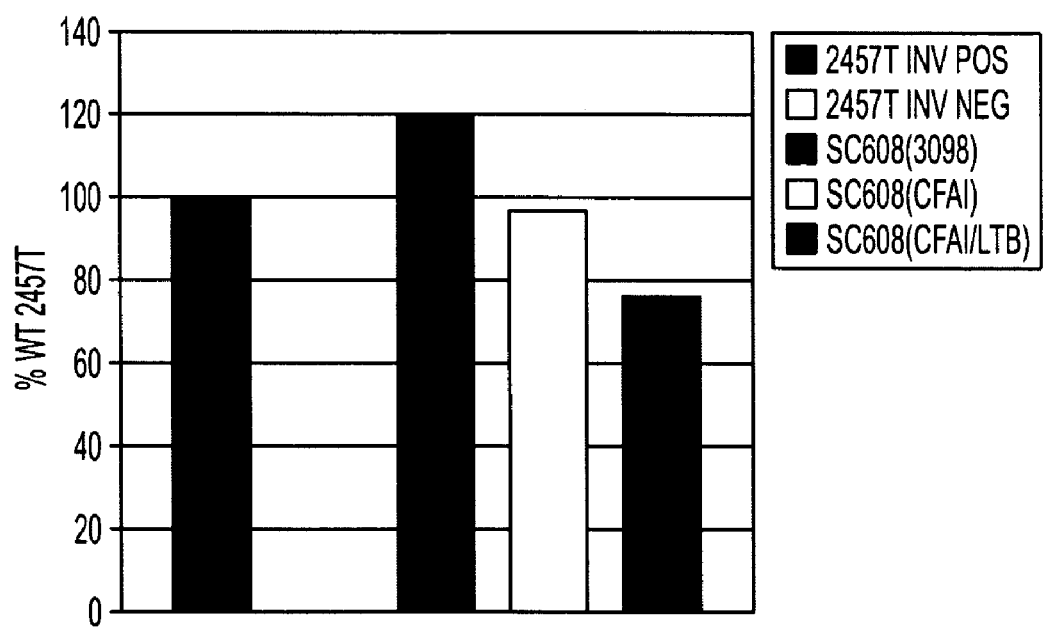
FIG. 2D shows a plot of the invasiveness as a percentage of a wild-type 2457T invasion positive isolate. 2547T Inv Pos indicates a congo red positive colony, while Inv negative indicates a congo red negative colony.
Figure 3A:
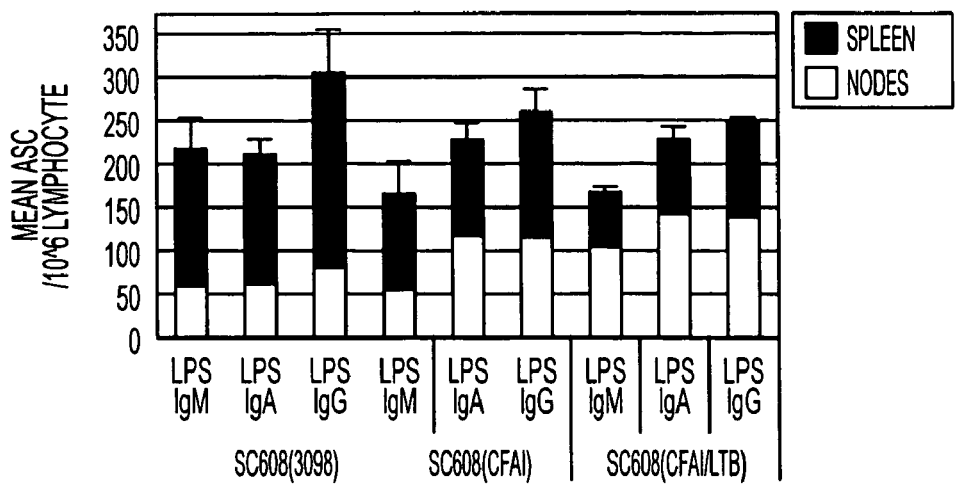
FIGS. 3 A, B, and C show antigen-specific antibody secreting cells (ASCs) from cervical lymph nodes (CLN) and splenocytes measured by ELISPOT analysis. One week after the second immunization spleens and cervical lymph nodes were harvested from 6 animals per vaccine group. Lymphocytes from individual animals were tested for response to the indicated antigen using a protocol described in Hartman, Van De Verg et al 1994. The results are given as a mean of ASC per $10^6$ lymphocyte. Error bars indicate the standard error for each group.
Figure 3B:
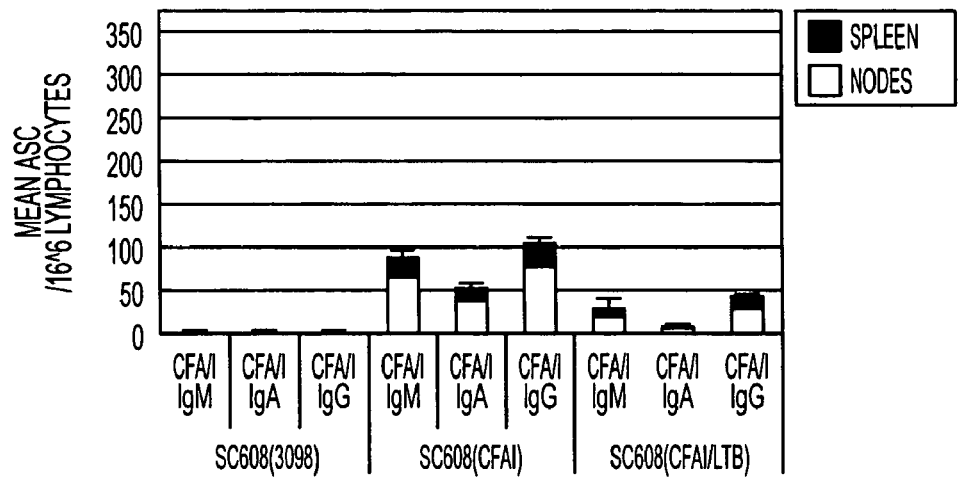
Figure 3C:
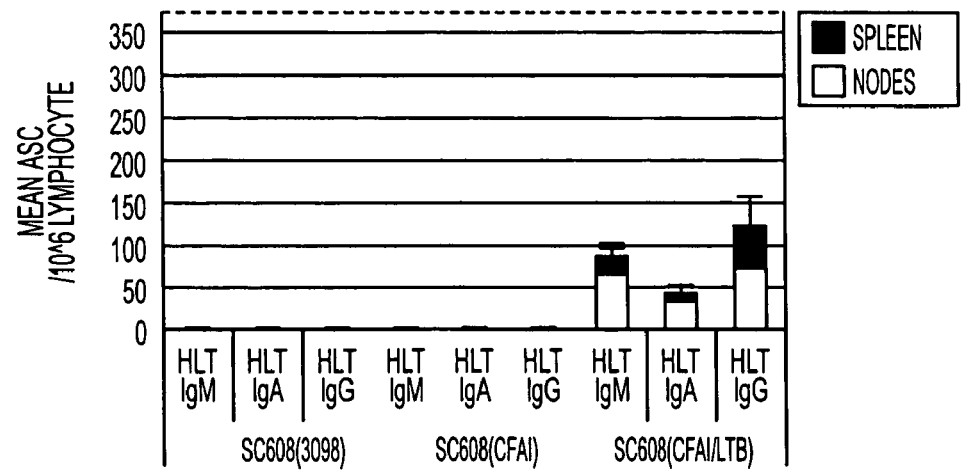

Evaluation of HeLa Cell Invasion Using *Shigella* Hybrid Vaccine Strains:

It is generally accepted that live attenuated strains of *Shigella* must retain the ability to invade nonphagocytic cells in order for them to generate protective immune responses the host. Thus, *Shigella* vaccine strains SC608(3098), SC608 (CFAI) and SC608(CFAI/LTB) were evaluated for invasiveness using the gentamicin protection assay in HeLa epithelial cells (10). The assay is based on the limited ability of the antibiotic gentamicin to penetrate eukaryotic cells (31). *Shigella* that invade and become intracellular are protected from the bactericidal effects of gentamicin, whereas extracellular organisms are killed. Positive and negative control strains for this assay are congo red positive and congo red negative isolates of the wild type *S. flexneri* strain 2457T. Congo red binding in *S. flexneri* is associated with virulence plasmid maintenance and thus infectivity (9, 26, 27). Results for the test strains are calculated as a percentage of the 2457T congo red positive isolate. Results from this assay indicate SC608 (3098) is slightly more invasive (120%) than 2457T, while SC608(CFAI) and SC608(CFAI/LTB) are slightly less invasive (96% and 75% respectively) (FIG. 2D). SC608(CfaAE) is also slightly less invasive (65%) (data not shown). Thus demonstrating that expression of ETEC antigens (CfaB CfaE and LTB) in SC608, do not appear to significantly affect HeLa cell invasion.

Figures 1, 4A:
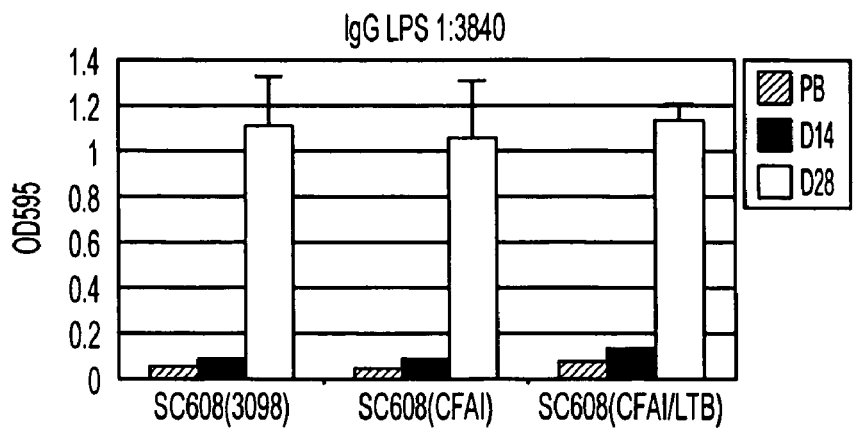
FIGS. 4 A, B and C show serum and mucosal antibody responses from guinea pigs immunized on days 0 and 14 with SC608 or its derivatives.
Figures 2, 4A:
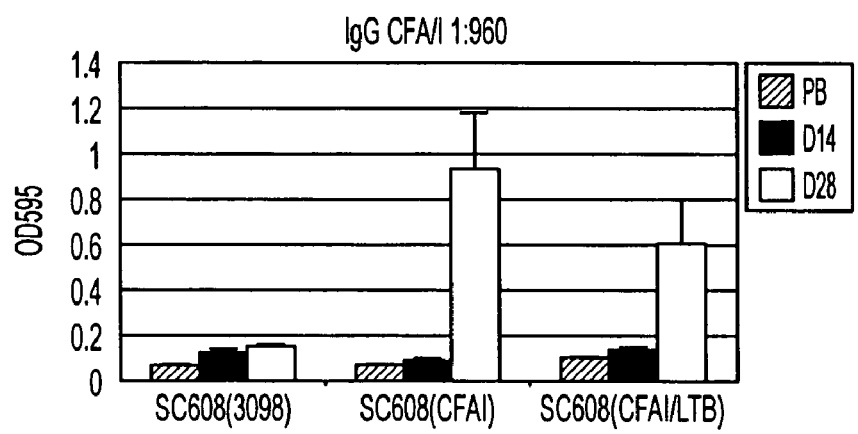
FIGS. 2 A, B, C and D show protein expression. Western blots of whole-cell extracts from *Shigella* vaccine strains expressing ETEC antigens.
Figures 3, 4A:
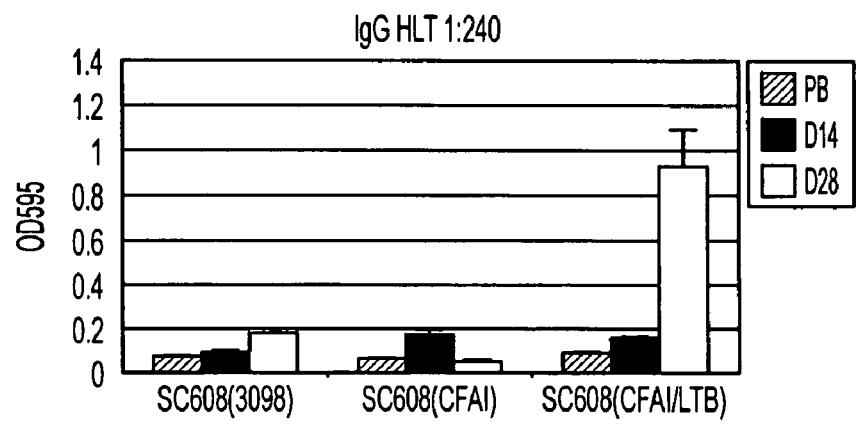

Evaluation of Immune Responses in Guinea Pigs Immunized with Hybrid Vaccine Strains:

The immunogenicity and protective efficacy of each vaccine strain was tested in guinea pigs. Fifty-six guinea pigs were separated into groups (14 animals per group) and intranasally immunized with 2 doses of SC608(3098), SC608 (CFAI), SC608(CFAI/LTB) and normal saline (unimmunized control animals), spaced 14 days apart. One week after the last immunization 6 guinea pigs per group were euthanized and an ELISPOT assay was used to detect local immune response to *Shigella* and ETEC antigens in the spleen and cervical lymph nodes (CLN). *S. flexneri* 2a LPS-specific IgG, IgA, and IgM antibody secreting cells (ASCs) were consistently detected and did not vary significantly between vaccine strains (FIG. 3, panel 1). ASCs were also measured using ETEC-derived antigens CFAA and HLT. Using intact CFA/I fimbriae as an antigen, ASC's were detected in both SC608 (CFAI) and SC608(CFAI/LTB) vaccinated animals with IgG being the dominant isotype detected (FIG. 3, panel 2). Interestingly, and for reasons that are not immediately apparent the CFA/I-specific ASCs for SC608(CFAI/LTB) were lower than in SC608(CFAI) immunized animals. As expected HLT-specific ASCs were detected for SC608(CFAI/LTB) only and again IgG dominated the isotype distribution (FIG. 3, panel 3).

Figures 1, 4B:
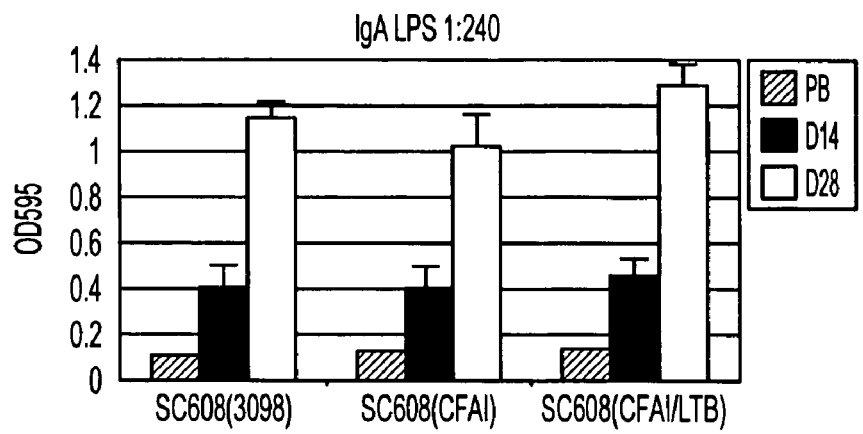
Figures 2, 4B:
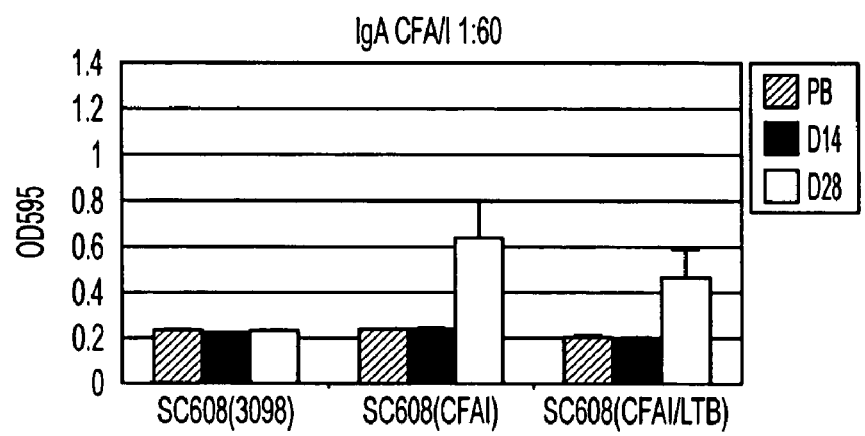
Figures 3, 4B:
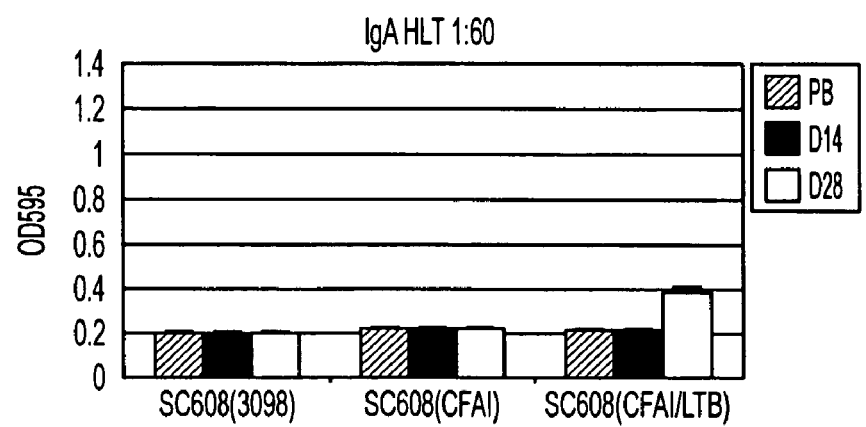

Immune responses in serum and mucosal secretions were measured using enzyme-linked immunosorbent assay (ELISA) on days 0, 14, 28. Serum IgG and IgA-specific immune responses were measured against *S. flexneri* 2a LPS, intact CFA/I fimbriae and HLT. Consistent with the ELISPOT assay all groups immunized with SC608 derivatives induced significant serum IgG and IgA LPS responses (FIG. 4A). Interestingly, only IgA-specific LPS responses were detected on day 14. Significant serum IgG responses were detected for SC608(CFAI) and SC608(CFAI/LTB) immunized animals, while serum IgA responses were less consistently detected (FIG. 4B). In fact serum IgA responses for HLT were marginal and only detected in some animal and was not considered significantly above background.

Figures 1, 4C:
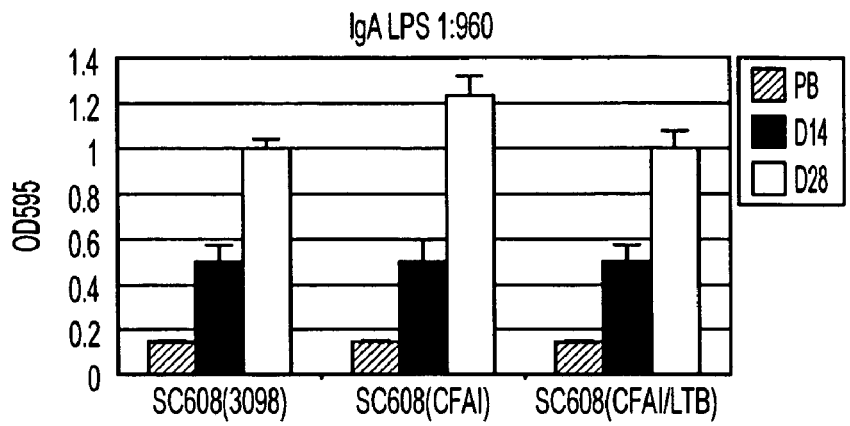
Figures 2, 4C:
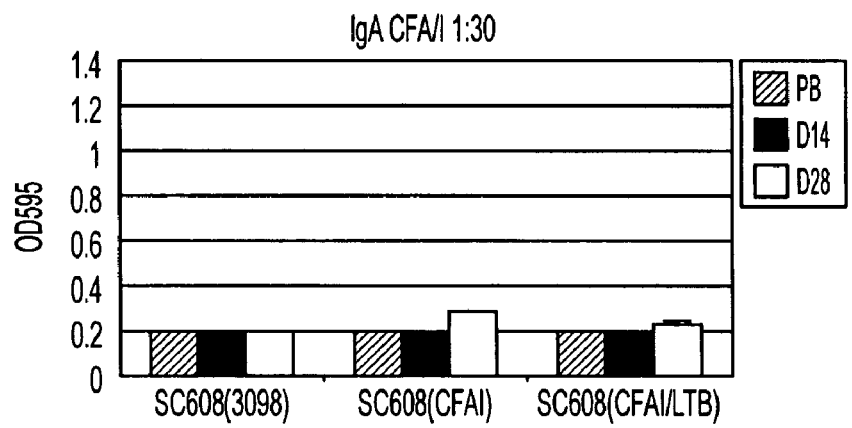
Figures 3, 4C:
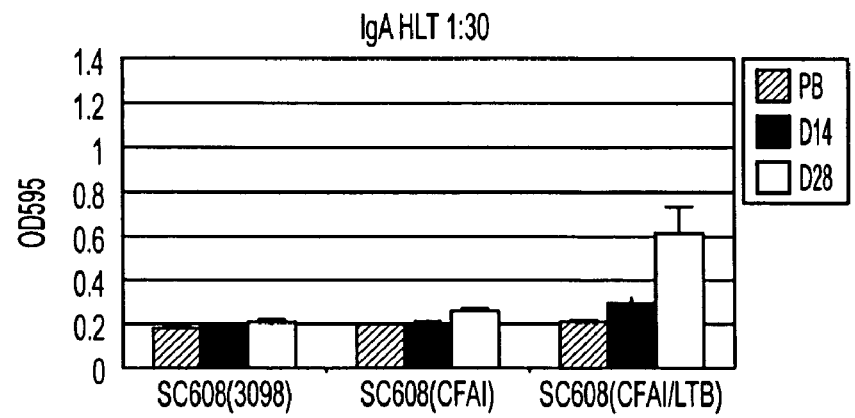

Mucosal immune responses were measured for LPS, CFA/I and HLT-specific secretory IgA (sIgA) from ocular washes. ELISA assays were used to quantitate sIgA antibodies with an initial starting dilution of 1:30. All animals immunized with SC608 vector had high levels of sIgA antibodies against *S. flexneri* LPS even at day 14 (FIG. 4C). sIgA antibodies specific for HLT were detected in animals vaccinated with SC608(CFAI/LTB), however no sIgA specific for CFA/I was detected for (SC608CFAI) vaccinated animals.

Challenge Assay:

All vaccinated guinea pigs as well as normal saline controls were challenged three weeks after the final immunization with homologous wild-type *Shigella* 2457T using the Sereny test. Guinea pigs (eight per group) were inoculated in the conjunctival sac of one eye for sham immunized and both eyes for SC608 immunized guinea pigs. All groups immunized with SC608 derivative were at least partially protected against disease (table 1).

TABLE 1

Protection Following Challenge with Wild-type *S. Flexneri* 2a 2457T

| Immunizing strain | No. of eyes inoculated | No. of eyes with the Indicated rating (a) | | | | Percent Protection (b) | | |
|---|---|---|---|---|---|---|---|---|
| | | 0 | 1 | 2 | 3 | F | P | C |
| Normal Saline | 8 | 0 | 1 | 1 | 6 | 0 | 12.5 | 0 |
| SC608/vector | 16 | 9 | 5 | 2 | 0 | 56.3 | 31.2 | 87.5 |
| SC608/CFAI | 16 | 13 | 3 | 0 | 0 | 81.3 | 18.7 | 100 |
| SC608/CFAI/LTB | 16 | 12 | 2 | 2 | 0 | 75.0 | 12.5 | 87.5 |

(a) Inflammation: 0 indicates no inflammation or mild disease, 1 indicates mild keratoconjunctivitis, 2 indicates keratoconjunctivitis without purulence, 3 indicates severe keratoconjunctivitis with purulence.
(b) F = Full, P = Partial, and C = Combined SC608/CFAI demonstrated the highest level of protection with 81.3% full protection and 18.7 partial protection.

Figure 5G:
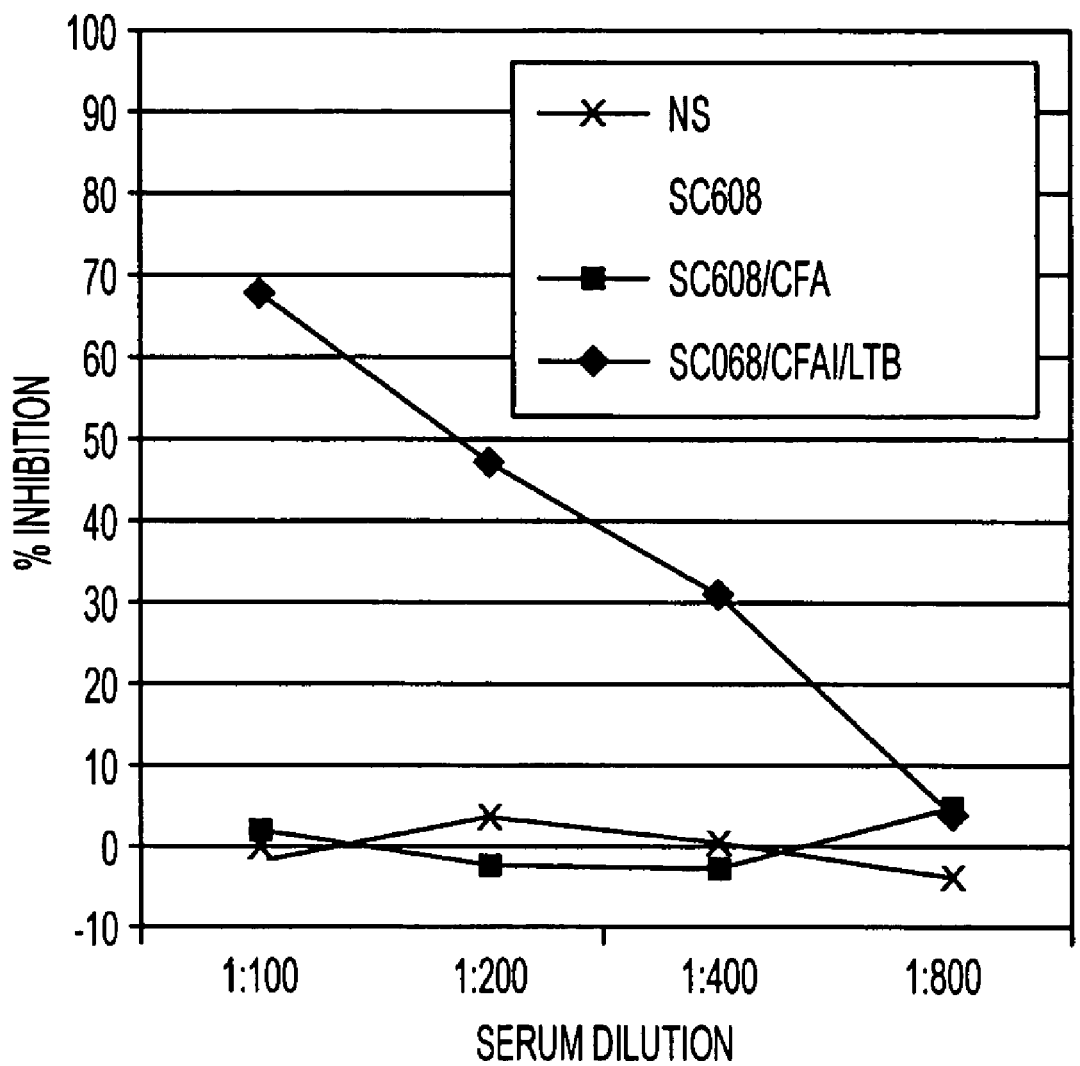
FIG. 5 A-G show the inhibition of heat-labile toxin (HLT)-mediated elongation by antiserum generated in animals immunized with SC608 or its derivatives.
FIG. 5C shows CHO cells treated with HLT mixed with pooled serum from guinea pig immunized with normal saline (NS).

Functional Evaluation of Antibodies Produced Against LTB Using CHO Cell Elongation Assay:

*E. coli* derived type I heat-labile toxin (HLT) is the prototypical $\alpha_1\beta_5$ enterotoxin that causes elevation of the intracellular levels of cyclic AMP (cAMP), resulting in watery diarrhea which is associated with ETEC infections (reviewed in (19). In vitro, HLT induces elongation of cultured Chinese hamster ovary (CHO-K1; ATCC CCL-61) cells most likely due to changes in the cytoskeleton as a result of high cAMP levels (29). We used this HLT-induced change in cellular morphology to measure the neutralizing properties of the antibodies induced by all SC608 derivatives. The minimal concentration of HLT needed maximal CHO cell elongation was determined to be 25 ng/ml. Serum collected from guinea pigs (eight per group) on day 28 was pooled using equal volumes and tested were for the ability to inhibit HLT elongation. Only serum from animal immunized with SC608 (CFAI/LTB) were able to inhibit HLT-mediated elongation (FIG. 5 A-F). In addition this affect could be titrated upon dilution of the serum thus demonstrating that antibodies raised against the B subunit of HLT can neutralize the toxic affects of HLT in vitro (FIG. 5G).

EXAMPLES

Bacterial Strains and Growth Conditions

SC608 *S. flexneri* 2a) is an aspartate semialdehyde dehydrogenase (Δasd) knockout of SC602 (6). SC608 lacks the asd gene and requires diaminopimelic acid (DAP) at a concentration of 50 µg/ml for growth. The endpoints of the asd deletion in SC608 have been mapped by sequencing the region.

Example 1

Plasmid Construction

The recombinant plasmid used for CfaB expression was constructed in a single step. PCR primers (CFA1-2, 5' GATCAAGCTTCCATGAAAAAGGAGGGATGTA SEQ ID NO 1 and CFA-9, 5' GATCCCATGGGCATGCATAAATTATTCTATTTACTAAGT SEQ ID NO 2) were used to amplify the cfaA and cfaB genes from genomic DNA of the CFA/I producing strain of enterotoxigenic *E. coli* (ETEC) H10407. The PCR product was digested with NcoI and HindIII and purified (Qiagen). The pYA3098 plasmid (gift Roy Curtiss III) was also digested using the same enzymes and purified (Qiagen). The fragments were ligated using T4 DNA ligase (NEB) and transformed into SC608 colonies were selected for on LB agar plates. Colonies containing the proper recombinant were verified by restriction digestion.

The recombinant plasmid used for CfaE expression was constructed in two steps. A DNA fragment containing the cfaA gene including the signal sequence, was amplified from ETEC strain H10407 genomic DNA using the PCR primers (5'-TACATGCCATGGATAAATTATTCTATTTACT-3' SEQ ID NO 3 and 5'-CGTTTATCCTTTATCATTCTCTTAG-TATATAGATGAGTAA-3' SEQ ID NO 8. A separate fragment containing the cfaE gene was amplified from the same template using the primers (5'-TTACTCATCTATATACTAA-GAGAATGATAAAGGATAAACG-3' SEQ ID NO 9 and 5'-TTCAGCCCAAGCTTTAGCGCCAATATGTTGTTAT-3' SEQ ID NO 10). Both PCR products were gel purified (Qiagen) and used in the second round of PCR to generate a fusion or single PCR product that consisted of the cfaA gene linked to the cfaE gene. The resulting PCR product was cut with NcoI and HindIII and purified (Qiagen). This fragment was ligated into pYA3098 cut with the same enzymes. The ligation was transformed into *E. coli* strain x6212 (12). Colonies containing the correct recombinant were identified by restriction digestion and transformed into SC608 by electroporation.

The recombinant plasmid used for CfaB and LTB expression was constructed in two steps. A DNA fragment containing the CfaA and CfaB genes, including the signal sequence, was amplified from ETEC strain H10407 genomic DNA using the PCR primers (5'-TACATGCCATGGATAAATTAT-TCTATTTACT-3' SEQ ID NO 3 and 5'-ATTCTGTTATATAT-GTCAACCTGCAGGAGGGATGTATAAACATACC-'3 SEQ ID NO 4). A separate fragment containing the LTB gene was amplified from the same template using the primers (5'-GGTATGTTTATACATCCCTCCTGCAGGT-TGACATATATAACAGAAT-3' SEQ ID NO 5 and 5'-TTAC-CCAAGCTTAGACATGCTTTTAAAGCAAA-3' SEQ ID NO 6). Both PCR products were gel purified (Qiagen) and used in the second round of PCR to generate a fusion or single PCR product that consisted of the CfaA and CfaB genes linked to the LTB gene. The resulting PCR product was cut with NcoI and HindIII and purified (Qiagen). This fragment was ligated into pYA3098 cut with the same enzymes. The ligation was transformed into *E. coli* strain x6212 (12). Colonies containing the correct recombinant were identified by restriction digestion and transformed into SC608 by electroporation.

Example 2

Protein Expression and Colony Blots

*Shigella* strains were grown to late log phase $OD_{600}$ 1.0-1.5 harvested by centrifugation in a Sorvall S6 4000 rpm for 7 min at 4° C. Bacterial pellets were resuspended in IX NuPage loading buffer (Invitrogen) and stored at −20 C. Lysates were prepared by sonicating pellets three separate times followed by boiling for 5 min. Protein samples were loaded on a 4-12% NuPage Bis-Tris Gel (Invitrogen) and electrophoresed for 1 hour at 180 V. Controls proteins, including purified *E. coli* derived heat-labile toxin (HLT) (Swiss Serum and Vaccine Institute, Berne Switerland) and purified CFA/I fimbriae (gift from Fred Cassels), were diluted to 50 and 200 ng/µl respectively and 5 µl was loaded along with bacterial lysates on a 4-12% NuPage Bis-Tris Gel. Gels were either stained with Coomassie Blue R-250 to check protein levels or were transferred to nitrocellulose membranes for western blot analysis. Blots were blocked in 2% casein (3.5 g/L NaCl, 0.58 g/L Tris-HCl, 20 g/L Casein, 1 g/L Sodium Azide) and incubated in primary antibody (anti-HLT, anti-CfaE and anti-CFA/I) for 1-14 h. Blots were washed three times using Tris-buffered saline (TBS) buffer (1.58 g/L Tris-HCl, 0.9 g/L NaCl, pH7.4). A proteinA-AP conjugate solution (Sigma) was diluted 1:500 in 2% casein and added to the blots for 1 hour. Blots were washed three times in TBS and developed using Naphthol/Fast red solution in 50 mM Tris-HCl pH 8.0 (Sigma).

For colony blots, Shigella vaccine strains were spotted to LB agar plates and grown 18 h at 37° C. Nitrocellulose membranes were placed on the plates and proteins were absorbed for 5 min at room temperature. Colonies were washed off the membrane using TBS, blocked in 2% casein, and incubated in primary antibody (anti-HLT, anti-CfaE and anti-CFA/I) for 1-14 h. Blots were washed three times using TBS (1.58 g/L Tris-HCl, 0.9 g/L NaCl, pH 7.4). A Protein A-AP conjugate solution (Sigma) was diluted 1:500 in 2% casein and added to the blots for 1 hour. Blots were washed again in TBS and developed using Naphthol/Fast red solution in 50 mM Tris-HCl pH 8.0 (Sigma).

Example 3

HeLa Cell Invasion Assays

HeLa gentamicin protection assays were performed as previously described with some minor modifications (10). HeLa cell (ATCC CCL-2) monolayers were grown semiconfluent in 75 cm$^2$ flasks in MEM complete (cMEM) containing 10% FBS, 2 mM L-glutamine, penicillin and streptomycin (180 µg/ml for both). One flask was trypsinized using 0.25% trypsin (Gibco) and the concentration of cells adjusted to $2 \times 10^5$ cells/ml in cMEM. 24-well plates were seeded with 2 mls HeLa cells and grown overnight at 37° C., 5% $CO_2$ to an approximate confluency of 90%. HeLa cells were washed and fresh cMEM was put on 2 hrs before the addition of bacteria. Log-phase cultures of bacteria (grown in LB) were added at an estimated multiplicity of infection of 10. After the addition of bacteria the 24-well plates were centrifuged in a Sorvall swinging bucket rotor at 3000 rpm for 10 min at 25° C. Plates were incubated at 37° C., 5% $CO_2$ for 1.5 hours. 24-well plates were washed three times with Hank's Balanced Salt Solution (Gibco) then incubated with cMEM containing gentamicin (50 µg/ml) for 2 hours at 37° C., 5% CO2. HeLa cells were lysed using a 0.1% Triton X-100 solution for 10 min. Bacteria were plated to LB agar plates and bacterial colonies were counted after growth at 37° C. for 18 hours.

Example 4

Immunizations and Challenge Assay

Shigella strains used for immunization were streaked to LB agar plates and grown to confluency for 24 hrs at 37° C. Bacteria were scraped off and resuspended in normal saline (NS) solution (0.9% w/v, NaCl). The concentration was adjusted to $2-5 \times 10^8$ CFU/ml using NS. Male Hartley guinea pigs 150-200 gm were sedated using a 2:1 mixture ketamine/xylazine and immunized intranasally with 50 µl of bacterial suspension per nare. Guinea pig immunizations were spaced two weeks apart. Three weeks after the last immunization animals were sedated as described above and $5 \times 10^8$ CFU of wild-type Shigella flexneri 2a 2457T in 25 µl NS was inoculated into each eye of immunized and only the left eye of unimmunized animals. Sereny reaction were monitored for 4 days and scored on day 3. 0 indicates no inflammation or mild disease, 1 indicated mild keratoconjunctivitis, 2 indicates keratoconjunctivitis with out purulence, 3 indicates severe keratoconjunctivitis with purulence. A score of 0 was considered complete protection and 1 was considered partial protection.

Example 5

Enzyme-Linked Immunosorbent Assays (ELISA)

Antigens used in ELISAs included purified S. flexneri 2a LPS, purified CFA/I fimbriae from ETEC strain H10407 (gift Fred Cassels), purified E. coli derived HLT (Swiss Serum and Vaccine Institute, Berne Switerland). Antigens were diluted in coating buffer (50 mM sodium carbonate, 30 mM sodium bicarbonate, pH 9.6) and allowed to absorb to 96-well plates (1 µg/well) overnight at 4° C. (Coster). Plates were blocked in 2% casein for 1 h at room temperature. Primary antibody derived from serum was obtained via ear prick of immunized guinea pigs. Primary antibody for mucosal secretion was obtained by washing the conjunctival sac of guinea pig eyes with 100 µl of PBS (10.75 mM sodium phosphate, 145 mM NaCl). Primary antibody was diluted in 2% casein and incubated with the antigen-coated plates for 1 h. After three washes in PBS with 0.05% Tween 20 (PBS-Tween), plates were probed with rabbit anti-guinea pig IgG alkaline phosphatase conjugate (diluted 1:1000 in 2% casein, Sigma Immunochemical) or rabbit anti-guinea pig IgA (diluted 1:800 in 2% casein, ICN Laboratories). Plates probing for IgA were washed in PBS-Tween and incubated with anti-rabbit IgG alkaline phosphatase conjugate (diluted 1:1000 in 2% casein, Sigma Immunochemical). After 1 h incubation with conjugated antibody, the plates were washed three times in PBS-Tween and 100 µl of BluePhos Microwell phosphatase substrate system (Kirkegaard & Perry). The $OD_{595}$ was measured on a Molecular Devices ELISA plate reader.

Example 6

Antibody Secreting Cell (ASC) Analysis

Animals were sacrificed by injection with sodium pentobarbital and spleens and cervical lymphnodes (CLN) were harvested and placed immediately in RPMI 1640 medium (GIBCO) containing 50 µg/ml gentamicin. Tissues were homogenized and the cell suspension was filtered through a sterile 70 µm screen to remove debris. Cells were washed once in RPMI 1640 medium containing 50 µg/ml gentamicin and the erythrocytes were lysed with erythrocyte lysis buffer (Sigma Chemical). Cells were washed an additional time with RPMI 1640 medium and finally resuspended complete RPMI 1640 (cRPMI) with 10% FBS, L-glutamine 2 mM, and 50 µg/ml of gentamicin at a concentration of $2.5 \times 10^6$ cells/ml.

The O-antigen-specific antibody secreting (ASC) cell response from splenocytes and cervical lymphocytes were determined as described in (14). Briefly, each 96-well microtiter plate (Nunc-Immuno Maxisorb plates) were coated as described in the ELISA procedure above and blocked using RPMI 1640 containing 5% FBS one hour prior to use. Immediately before use, plates were washed three times using PBS. Cell suspension was dispensed and the plates were incubated overnight at 37° C., 5% $CO_2$. After incubation plates were washed four times with PBS-Tween and rabbit anti-guinea pig IgG, IgA, or IgM (diluted in 2% casein at 1:1200, 1:800, 1:800 respectively, ICN Laboratories) was added and incubated 2 h. After incubation plates were washed three times in PBS-Tween, and anti-rabbit IgG alkaline phosphatase conjugate (Sigma Immunochemical) was added at a dilution of 1:1200 in 2% casein. After a 2 h incubation plates were washed three times with PBS-Tween and a melted agarose substrate overlay (0.7% type I, low-EEO agarose) containing BCIP and NBT was added. Antigen-specific ASCs were visualized and counted using a stereomicroscope.

Example 7

Heat-Labile Toxin Inhibition Assay

Heat-labile toxin (HLT) inhibition was assessed by the extent of Chinese Hamster Ovary (CHO) cell elongation in the presence of HLT essentially as described in (29). CHO cells (ATCC CCR-61) were maintained in complete DMEM (cDMEM) containing 2 mM L-glutamine, 10% FBS, penicillin and streptomycin (180 µg/ml for both) at 37° C., 5% $CO_2$. Semi-confluent monolayers grown in T75 $cm^2$ flasks were trypsinized using 0.25% Trypsin (Gibco) and the concentration was adjusted to $8.75 \times 10^4$. To determine the lowest concentration for maximum CHO cell elongation, heat-labile toxin (HLT) purified from *E. coli* (Swiss Serum and Vaccine Institute, Berne Switerland) was serially diluted in PBS, pH7.2 (Gibco) and added directly to 1 ml aliquots of trypsinized CHO cells in 4-well chamber slides. The slides were grown for 20 hrs at 37° C., 5% $CO_2$. The cells were fixed with methanol and stained with Giemsa and 3 fields per concentration were photographed under 10× magnification. A concentration of 25 ng/ml was chosen for neutralization experiments. Serum used for inhibition assay was prepared by pooling equal volumes of serum collected on day 28 from each vaccination group (8 guinea pigs per group). Inhibition of HLT-mediated elongation was determined by incubating serially diluted serum (10 µl) in the presence of HLT (25 ng/ml final concentration) at 37° C. for 30 min in a volume of 100 µl. Toxin-antiserum mixtures were added to trypsinized CHO cells and assayed for elongation as described above. The minimum dilution used for inhibition was 1:100.

For calculation of the extent of inhibition, CHO cell elongation resulting from 25 ng/ml of HLT (which usually caused 88-90% elongation) was taken as zero and the percent elongation in the absence of toxin (which was around 15-20%) was taken as 100% inhibition.

REFERENCES

1. Altboum, Z., E. M. Barry, G. Losonsky, J. E. Galen, and M. M. Levine. 2001. Attenuated *Shigella flexneri* 2a Delta guaBA strain CVD 1204 expressing enterotoxigenic *Escherichia coli* (ETEC) CS2 and CS3 fimbriae as a live mucosal vaccine against *Shigella* and ETEC infection. Infect Immun 69:3150-8.
2. Altboum, Z., M. M. Levine, J. E. Galen, and E. M. Barry. 2003. Genetic characterization and immunogenicity of coli surface antigen 4 from enterotoxigenic *Escherichia coli* when it is expressed in a *Shigella* live-vector strain. Infect Immun 71:1352-60.
3. Anderson, R. J., M. F. Pasetti, M. B. Sztein, M. M. Levine, and F. R. Noriega. 2000. DeltaguaBA attenuated *Shigella flexneri* 2a strain CVD 1204 as a *Shigella* vaccine and as a live mucosal delivery system for fragment C of tetanus toxin. Vaccine 18:2193-202.
4. Barry, E. M., Z. Altboum, G. Losonsky, and M. M. Levine. 2003. Immune responses elicited against multiple enterotoxigenic *Escherichia coli* fimbriae and mutant LT expressed in attenuated *Shigella* vaccine strains. Vaccine 21:333-40.
5. Barzu, S., J. Arondel, S. Guillot, P. J. Sansonetti, and A. Phalipon. 1998. Immunogenicity of IpaC-hybrid proteins expressed in the *Shigella flexneri* 2a vaccine candidate SC602. Infect Immun 66:77-82.
6. Barzu, S., A. Fontaine, P. Sansonetti, and A. Phalipon. 1996. Induction of a local anti-IpaC antibody response in mice by use of a *Shigella flexneri* 2a vaccine candidate: implications for use of IpaC as a protein carrier. Infect Immun 64:1190-6.
7. Coster, T. S., C. W. Hoge, L. L. VanDeVerg, A. B. Hartman, E. V. Oaks, M. M. Venkatesan, D. Cohen, G. Robin, A. Fontaine-Thompson, P. J. Sansonetti, and T. L. Hale. 1999. Vaccination against shigellosis with attenuated *Shigella flexneri* 2a strain SC602. Infect Immun 67:3437-43.
8. Curtiss, R., 3rd, K. Nakayama, and S. M. Kelly. 1989. Recombinant avirulent *Salmonella* vaccine strains with stable maintenance and high level expression of cloned genes in vivo. Immunol Invest 18:583-96.
9. Daskaleros, P. A., and S. M. Payne. 1987. Congo red binding phenotype is associated with hemin binding and increased infectivity of *Shigella flexneri* in the HeLa cell model. Infect Immun 55:1393-8.
10. Elsinghorst, E. A. 1994. Measurement of invasion by gentamicin resistance. Methods Enzymol 236:405-20.
11. Evans, D. G., T. K. Satterwhite, D. J. Evans, Jr., and H. L. DuPont. 1978. Differences in serological responses and excretion patterns of volunteers challenged with enterotoxigenic *Escherichia coli* with and without the colonization factor antigen. Infect Immun 19:883-8.
12. Galan, J. E., K. Nakayama, and R. Curtiss, 3rd. 1990. Cloning and characterization of the asd gene of *Salmonella typhimurium*: use in stable maintenance of recombinant plasmids in *Salmonella* vaccine strains. Gene 94:29-35.
13. Hale, T. L. 1991. Genetic basis of virulence in *Shigella* species. Microbiol. Rev 55:206-24.
14. Hartman, A. B., L. L. Van de Verg, H. H. Collins, Jr., D. B. Tang, N, O. Bendiuk, D. N. Taylor, and C. J. Powell. 1994. Local immune response and protection in the guinea pig keratoconjunctivitis model following immunization with *Shigella* vaccines. Infect Immun 62:412-20.
15. Jennison, A. V., and N. K. Verma. 2004. *Shigella flexneri* infection: pathogenesis and vaccine development. FEMS Microbiol Rev 28:43-58.
16. Jordi, B. J., G. A. Willshaw, B. A. van der Zeijst, and W. Gaastra. 1992. The complete nucleotide sequence of region 1 of the CFA/I fimbrial operon of human enterotoxigenic *Escherichia coli*. DNA Seq 2:257-63.
17. Kang, H. Y., and R. Curtiss, 3rd. 2003. Immune responses dependent on antigen location in recombinant attenuated *Salmonella typhimurium* vaccines following oral immunization. FEMS Immunol Med Microbiol 37:99-104.
18. Kang, H. Y., J. Srinivasan, and R. Curtiss, 3rd. 2002. Immune responses to recombinant pneumococcal PspA antigen delivered by live attenuated *Salmonella enterica* serovar typhimurium vaccine. Infect Immun 70:1739-49.
19. Kaper, J. B., J. P. Nataro, and H. L. Mobley. 2004. Pathogenic *Escherichia coli*. Nat Rev Microbiol 2:123-40.
20. Katz, D. E., T. S. Coster, M. K. Wolf, F. C. Trespalacios, D. Cohen, G. Robins, A. B. Hartman, M. M. Venkatesan, D. N. Taylor, and T. L. Hale. 2004. Two studies evaluating the safety and immunogenicity of a live, attenuated *Shigella flexneri* 2a vaccine (SC602) and excretion of vaccine organisms in North American volunteers. Infect Immun 72:923-30.
21. Koprowski, H., 2nd, M. M. Levine, R. J. Anderson, G. Losonsky, M. Pizza, and E. M. Barry. 2000. Attenuated *Shigella flexneri* 2a vaccine strain CVD 1204 expressing colonization factor antigen I and mutant heat-labile enterotoxin of enterotoxigenic *Escherichia coli*. Infect Immun 68:4884-92.

22. Mollenkopf, H., G. Dietrich, and S. H. Kaufmann. 2001. Intracellular bacteria as targets and carriers for vaccination. Biol Chem 382:521-32.

23. Noriega, F. R., G. Losonsky, J. Y. Wang, S. B. Formal, and M. M. Levine. 1996. Further characterization of delta aroA delta virG *Shigella flexneri* 2a strain CVD 1203 as a mucosal *Shigella* vaccine and as a live-vector vaccine for delivering antigens of enterotoxigenic *Escherichia coli*. Infect Immun 64:23-7.

24. Noriega, F. R., J. Y. Wang, G. Losonsky, D. R. Maneval, D. M. Hone, and M. M. Levine. 1994. Construction and characterization of attenuated delta aroA delta virG *Shigella flexneri* 2a strain CVD 1203, a prototype live oral vaccine. Infect Immun 62:5168-72.

25. Prevost, M. C., M. Lesourd, M. Arpin, F. Vernel, J. Mounier, R. Hellio, and P. J. Sansonetti. 1992. Unipolar reorganization of F-actin layer at bacterial division and bundling of actin filaments by plastin correlate with movement of *Shigella flexneri* within HeLa cells. Infect Immun 60:4088-99.

26. Sakai, T., C. Sasakawa, S. Makino, K. Kamata, and M. Yoshikawa. 1986. Molecular cloning of a genetic determinant for Congo red binding ability which is essential for the virulence of *Shigella flexneri*. Infect Immun 51:476-82.

27. Sasakawa, C., K Kamata, T. Sakai, S. Y. Murayama, S. Makino, and M. Yoshikawa. 1986. Molecular alteration of the 140-megadalton plasmid associated with loss of virulence and Congo red binding activity in *Shigella flexneri*. Infect Immun 51:470-5.

28. Szakal, D., I. Gado, and T. Pal. 2001. A colony blot immunoassay to detect enteroinvasive *Escherichia coli* and *Shigella* in water samples. J Appl Microbial 90:229-36.

29. Tsuji, T., T. Honda, and T. Miwatani. 1984. Comparison of effects of nicked and unnicked *Escherichia coli* heat-labile enterotoxin on Chinese hamster ovary cells. Infect Immun 46:94-7.

30. Turbyrill, K R., A. B. Hartman, and E. V. Oaks. 2000. Isolation and characterization of a *Shigella flexneri* invasin complex subunit vaccine. Infect Immun 68:6624-32.

31. Vaudaux, P., and F. A. Waldvogel. 1979. Gentamicin antibacterial activity in the presence of human polymorphonuclear leukocytes. Antimicrob Agents Chemother 16:743-9.

32. Weiss, S., and S. Krusch. 2001. Bacteria-mediated transfer of eukaryotic expression plasmids into mammalian host cells. Biol Chem 382:533-41.

33. Wu, S., D. W. Pascual, J. L. VanCott, J. R. McGhee, D. R. Maneval, Jr., M. M. Levine, and D. M. Hone. 1995. Immune responses to novel *Escherichia coli* and *Salmonella typhimurium* vectors that express colonization factor antigen I (CFA/I) of enterotoxigenic *E. coli* in the absence of the CFA/I positive regulator cfaR. Infect Immun 63:4933-8.

34. Svennerholm, A. M. and D. Steele. 2004. Progress in Enteric Vaccine Development. Best Prac. Res. Clin. Gastroenterol. 18:421-45.

All of the references referred to above are hereby incorporated by reference in their entirety.

While the invention has been described in detail, and with reference to specific embodiments thereof, it will be apparent to one of ordinary skill in the art that various changes and modifications can be made therein without departing from the spirit and scope thereof.

We claim:

1. Primer pairs characterized as having a length of about 15-100 nucleotides, which pairs permit the PCR amplification of the entire CfaA, CfaB and CfaE open reading frames without the entire CFA/I operon but with the signal sequence of each protein along with restriction sites for insertion into a vector which insertion allows for expression, export and assembly of the protein on the bacterial surface, which pairs contain sequences or sequences strictly complementary thereto and are selected from the group consisting of:
   a) 5'-GATCAAGCTTCCATGAAAAAGGAGGGATGTA-3' SEQ ID NO 1 and 5'-GATCCCATGGGCATGCATAAATTATTCTATTTACTAAGT-3' SEQ ID NO 2,
   b) 5'-TACATGCCATGGATAAATTATTCTATTTACT-3' SEQ ID NO 3 and 5'-ATTCTGTTATATATGTCAACCTGCAGGAGGGATGTATAAACATACC-'3 SEQ ID NO 4,
   c) 5'-GGTATGTTTATACATCCCTCCTGCAGGTTGACATATATAACAGAAT-3' SEQ ID NO 5 and 5'-TTACCCAAGCTTAGACATGCTTTTAAAGCAAA-3' SEQ ID NO 6 and
   d) 5'-TACATGCCATGGATAAATTATTCTATTTACT-3' SEQ ID NO 7 and 5'-CGTTTATCCTTTATCATTCTCTTAGTATATAGATGAGTAA-3' SEQ ID NO 8,
   e) 5'-TTACTCATCTATATACTAAGAGAATGATAAAGGATAAACG-3' SEQ ID NO 9 and 5'-TTCAGCCCAAGCTTTAGCGCCAATATGTTGTTAT-3' SEQ ID NO 10.

2. The primers of claim 1 wherein the sequences are selected from:
   a) 5'-GATCAAGCTTCCATGAAAAAGGAGGGATGTA-3' [SEQ ID NO 1] and 5'-GATCCCATGGGCATGCATAAATTATTCTATTTACTAAGT-3' [SEQ ID NO 2]
   b) 5'-TACATGCCATGGATAAATTATTCTATTTACT-3' [SEQ ID NO 3] and 5'-ATTCTGTTATATATGTCAACCTGCAGGAGGGATGTATAAACATACC-'3 [SEQ ID NO 4],
   c) 5'-GGTATGTTTATACATCCCTCCTGCAGGTTGACATATATAACAGAAT-3' [SEQ ID NO 5] and 5'-TTACCCAAGCTTAGACATGCTTTTAAAGCAAA-3' [SEQ ID NO 6] and
   d) 5'-TACATGCCATGGATAAATTATTCTATTTACT-3' [SEQ ID NO 7] and 5'-CGTTTATCCTTTATCATTCTCTTAGTATATAGATGAGTAA-3' [SEQ ID NO 8];
   e) 5'-TTACTCATCTATATACTAAGAGAATGATAAAGGATAAACG-3' [SEQ ID NO 9] and 5'-TTCAGCCCAAGCTTTAGCGCCAATATGTTGTTAT-3' [SEQ ID NO 10].

3. An expression plasmid comprising a cis-acting DNA promoter operably linked to an open reading frame containing enterotoxigenic *Escherichia coli* (ETEC) genes selected from the group consisting of cfaA, cfaB, cfaE, LTh B and combinations thereof, wherein expression occurs in the periplasmic space of a bacteria and the expressed protein is exported and assembled on the bacterial surface and the plasmid is derived from pYA3098.

4. The plasmid according to claim 3, wherein the cis acting promoter is Ptrc.

5. The plasmid comprises pCFA, pCFAI/LTB or pCfaAE.

6. The vector according to claim 3 further comprising the cfaABCE gene cluster from enterotoxigenic *E. coli* H10407.

7. The plasmid according to claim 3 wherein the open reading frame contains a combination of the cfaA and cfaB, cfaE and/or LTh B genes.

8. The plasmid according to claim 3 wherein the open reading frame contains a DNA fragment obtained by the PCR amplification and primers selected from the group consisting of:
   a) 5'-GATCAAGCTTCCATGAAAAAGGAGGGATGTA-3' [SEQ ID NO 1] and 5'-GATCCCATGGGCATGCATAAATTATTCTATTTACTAAGT-3' [SEQ ID NO 2],
   b) 5'-TACATGCCATGGATAAATTATTCTATTTACT-3' [SEQ ID NO 3] and 5'-ATTCTGTTATATATGTCAACCTGCAGGAGGGATGTATAAACATACC-'3 [SEQ ID NO 4],
   c) 5'-GGTATGTTTATACATCCCTCCTGCAGGTTGACATATATAACAGAAT-3' [SEQ ID NO 5] and 5'-TTACCCAAGCTTAGACATGCTTTTAAAGCAAA-3'[SEQ ID NO 6] and
   d) 5'-TACATGCCATGGATAAATTATTCTATTTACT-3' [SEQ ID NO 7] and 5'-CGTTTATCCTTTATCATTCTCTTAGTATATAGATGAGTAA-3' [SEQ ID NO 8], and
   e) 5'-TTACTCATCTATATACTAAGAGAATGATAAAGGATAAACG-3' [SEQ ID NO 9] and 5'-TTCAGCCCAAGCTTTAGCGCCAATATGTTGTTAT-3' [SEQ ID NO 10].

* * * * *